United States Patent [19]
Bokros et al.

[11] Patent Number: 5,628,791
[45] Date of Patent: May 13, 1997

[54] PROSTHETIC TRILEAFLET HEART VALVE

[75] Inventors: Jack C. Bokros; Jonathan C. Stupka, both of Austin, Tex.

[73] Assignee: Medical Carbon Research Institute, LLC, Austin, Tex.

[21] Appl. No.: 647,000

[22] Filed: May 9, 1996

[51] Int. Cl.⁶ .................................................. A61F 2/24
[52] U.S. Cl. ................................................... 623/2
[58] Field of Search ........................ 623/2, 900, 3; 600/16

[56] References Cited

U.S. PATENT DOCUMENTS

| | | |
|---|---|---|
| 4,373,216 | 2/1993 | Klawitter. |
| 4,451,937 | 6/1984 | Klawitter. |
| 4,820,299 | 4/1989 | Perrier, Sr. et al. ............... 623/2 |
| 4,822,353 | 4/1989 | Bokros ............................... 623/2 |
| 5,123,918 | 6/1992 | Perrier, Sr. et al. ............... 623/2 |
| 5,207,707 | 5/1993 | Gourley ............................. 623/2 |

OTHER PUBLICATIONS

M. Knoch, et al., "Flow Characteristics of Six Mechanical Heart Valve Prostheses in Aortic Position: Design Related Model Studies". *Surgery For Heart Valve Disease* (1990), 12 pgs.

*Primary Examiner*—David H. Willse
*Attorney, Agent, or Firm*—Fitch, Even, Tabin & Flannery

[57] ABSTRACT

A trileaflet heart valve includes a generally annular valve body having an interior wall of nominally circular cross-section into which 3 wedge-shaped projections radially extend to provide 3 pairs of flanking flat surfaces between which leaflets are pivotally supported and which includes an outwardly flaring upstream entrance end that, together with an elongated axial length, assures streamlined flow and a low transvalvular pressure drop. The leaflets assume an orientation substantially parallel to the central axis in the open position with their swinging movement in the direction of closing being guided by pairs of arcuate ridges and posts which protrude from the flanking flat walls of the projections and which guide the leaflets in a pivoting and translating swinging movement. The downstream ends of the curved ridges are enlarged in cross-section, compared to the upstream ends, and in combination with the posts create stops which determine the desired open position orientation of the three leaflets.

16 Claims, 6 Drawing Sheets

PROSTHETIC TRILEAFLET HEART VALVE

FIELD OF THE INVENTION

The present invention relates to mechanical heart valve prostheses and, in particular, to an improved trileaflet prosthetic heart valve having valve members or leaflets which can open to a substantially parallel position relative to the centerline of the central passageway and have pivot arrangements that assure reliable and responsive operation.

BACKGROUND OF THE INVENTION

A wide variety of mechanical heart valve prostheses have been developed to operate hemodynamically, in conjunction with the pumping action of the heart, which are designed to take the place of defective or diseased natural valves. These valves typically have valve bodies which accommodate valve members either in the form of a single occluder or in the form of multiple occluders or leaflets, wherein these valve members generally pivot along eccentric axes to open and close a central blood flow passageway through the valve body. Alternatively, some mechanical valves utilize valve members that both pivot and translate to open and close a central blood flow passageway.

In its open position, a prosthetic heart valve desirably provides a central blood flow passageway which is large and which has good flow characteristics so that blood flows freely therethrough without adverse boundary layer separation and with a minimum of drag. A heart valve mounted in the aortic position should be very responsive to blood flow so as to open quickly during the pumping stroke of the heart and to close quickly when the associated chamber of the heart relaxes so as to prevent substantial regurgitation of the blood. The opening and closing of the valve should be sufficiently soft so that the patient is not disturbed by the sounds produced and so that the impacts on the valve body are minimal. The heart valve must be made of materials that are biocompatible and thromboresistant, and in this regard, it is important that all surfaces be well washed by blood to prevent regions of stagnation which might lead to eventual clotting. Furthermore, the action of the valve should be such that it does not cause hemolysis (damaging of blood cells), and of course, the heart valve should be constructed to withstand countless openings and closures without the valve members jamming or escaping.

Prior art multi-leaflet heart valves have offered a variety of designs and configurations intended to address the some of the aforementioned problems. For example, U.S. Pat. No. 4,272,854 (Jun. 16, 1981) shows an early version of a bileaflet heart valve having an ear extending from each lateral side of each leaflet, which ear pivots in a recess, guided in part by a knob traveling in a longitudinal slot that is cut more deeply into the sidewall of the valve body.

U.S. Pat. No. 4,363,142 (Dec. 14, 1982) discloses a bileaflet heart valve wherein the leaflets have laterally extending ears in the form of generally oval or spherical projections that are received in recesses of complementary design.

U.S. Pat. No. 4,373,216 (Feb. 15, 1983) discloses a bileaflet heart valve wherein protrusions, extending generally radially inward from a pair of flat sidewall sections of the valve body, guide valve members which have slots in their lateral edges which fit about such protrusions. U.S. Pat. No. 4,451,937, (Jun. 5, 1984) shows a generally similar bileaflet heart valve where the pivot arrangement is formed with a reversal of parts wherein the leaflets have laterally protruding ears which are received within slots in the valve body sidewall that guide the opening and closing movements.

U.S. Pat. No. 4,308,624 (Jan. 5, 1982) discloses heart valves of both the single occluder and bileaflet type having curved valve members which both rotate and translate in moving between the open and closed positions, being guided by laterally extending ears that travel in slots. Later versions of this valve are disclosed in U.S. Pat. No. 4,357,715 wherein an elongated depression within each slot in the valve sidewall controls lateral movement within the slot, and also in U.S. Pat. No. 4,443,894 (Apr. 24, 1984) wherein the slots are of kidney bean shape.

U.S. Pat. No. 4,808,180 (Feb. 28, 1989) discloses a bileaflet valve wherein the leaflets each have a semi-conical shape and thus inherently provide significant resistance to blood flow through the valve in the open position. The leaflets are guided by generally C-shaped rails that protrude from the valve body sidewall and are received in recesses of complementary shape in the lateral edges of the semi-conical leaflets.

U.S. Pat. No. 5,207,707 (Jan. 16, 1992) discloses a trileaflet heart valve wherein the leaflets translate between open and closed positions guided by ears 74 which travel along curved grooves 40 situated within walls of a pivot structure 26. U.S. Pat. Nos. 4,820,299 and 5,123,918 also disclose trileaflet prosthetic heart valves, with the latter illustrating a construction wherein specially configured arcuate members protrude from the interior valve body surface and guide such leaflets in moving between the open and closed positions.

Commercially developed heart valves, such as the St. Jude Medical valve, have generally employed valve members oriented at a significant angle to the valve centerline in the open position, so that the backflow of blood preferentially impinges strongly upon the outflow surfaces of each valve member in order to initially impart a strong pivotal force component in the direction of closing movement. It is now felt to be particularly important that a mechanical heart valve prosthesis should provide a passageway through which blood can freely flow in the open position with a minimum of drag. To accomplish this desired objective, it is now believed that the valve members should be able to follow the flow and, when required, assume orientations which are generally parallel to the longitudinal axis of the passageway.

In summary, trileaflet heart valves should have such improved flow characteristics in the open position, should be reliable and responsive in leaflet movement and should be designed to avoid the likelihood of clotting. Trileaflet heart valves which meet these criteria continue to be sought.

SUMMARY OF THE INVENTION

The present invention provides mechanical trileaflet heart valve prostheses having the aforementioned desirable characteristics wherein the three valve members can assume an open position orientation substantially parallel to the longitudinal axis of the valve passageway when blood flow is at its highest.

The valve members are supported within the surrounding valve bodies by curved ridges which protrude from otherwise flat wall surfaces of wedge-shaped projections, which ridges are received within arcuate notches formed in the lateral edge surfaces of the leaflets. The ridges guide the valve members in pivotal and translational movement between the closed position and the open position wherein the valve members have a substantially parallel orientation to the longitudinal axis of the central passageway through the valve body.

These pivot arrangements are constructed so as to inhibit any possibility that the valve members may jam or stick during opening and closing travel along the curved ridges, and they include a pair of short posts located upstream of the upstream ends of the curved ridges against which the inflow surfaces of the valve members abut in the open position orientation. The downstream ends of the ridges are formed so as to interengage with the notches in the lateral edges of the valve members so as to serve as a stop for the valve members when each reaches its fully open position. When normal blood flow through the valve reverses, there is a component of force of blood flow impinging against the outflow surfaces that promotes pivoting movement toward the closed position. However, the shape and orientation of the ridges is such that, when the drag force of the reverse flow of blood against the leaflets is pushing the leaflets directly upstream, the downstream portions of the notches engage the downstream surface portions of the ridges which, because of their angular orientation to the valve centerline, create a camming effect which adds a significant component of force tending to pivot the leaflet in the direction of closing movement.

DETAILED DESCRIPTION OF THE PREFERRED EMBODIMENTS

Figure 1:
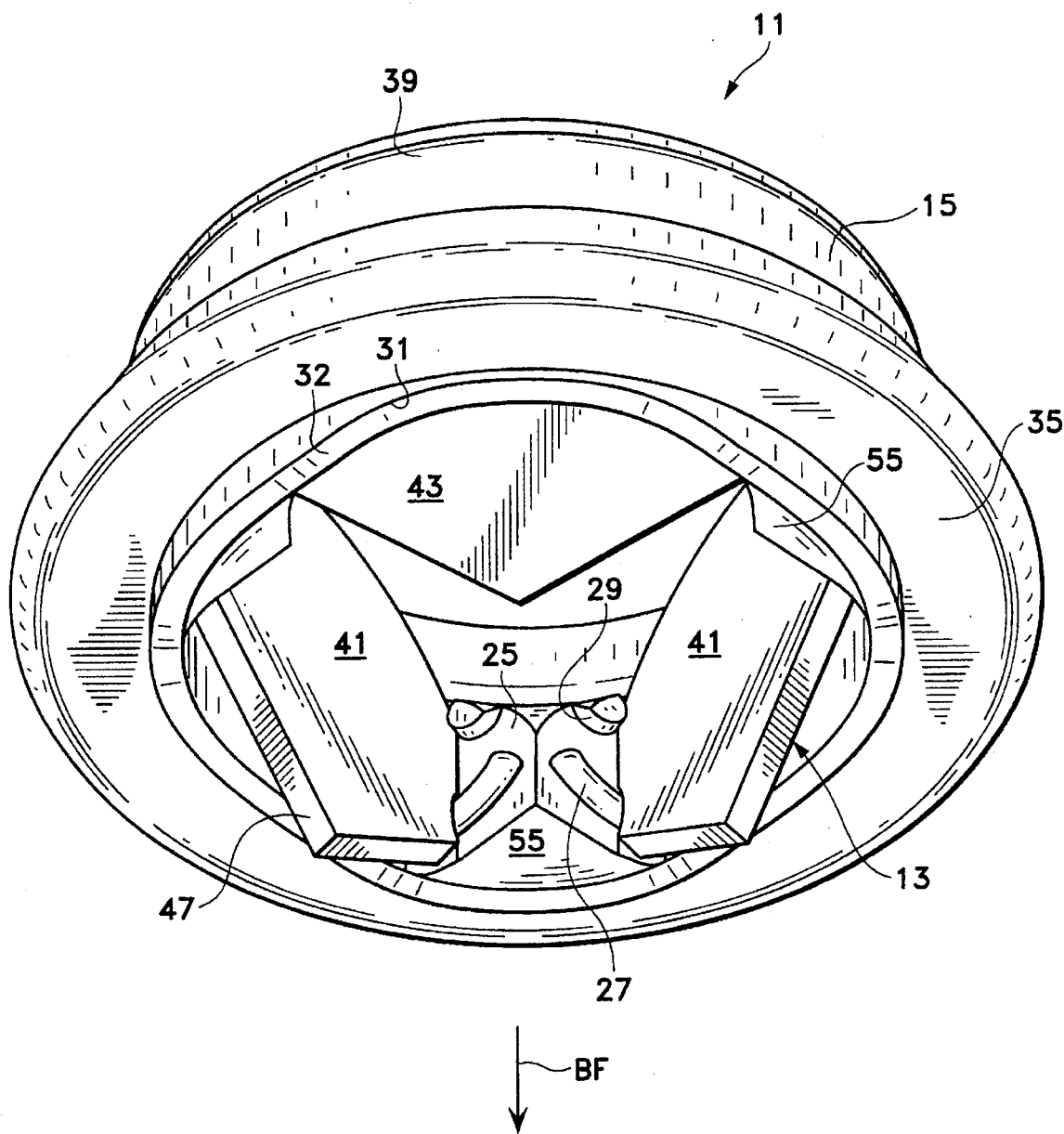
FIG. 1 is a perspective view of a trileaflet prosthetic heart valve embodying various features of the present invention, as viewed from a downstream orientation with the leaflets in the open position.

Illustrated in FIG. 1 is a prosthetic heart valve 11 which embodies various features of the present invention. Heart valves of this construction exhibit improved flow characteristics as a result of relatively low pressure drops across the valve; moreover, the valve bodies in combination with the leaflets substantially reduce boundary layer separation while also providing good washing characteristics which effectively avoid regions of stagnation and potential clotting. In addition, the pivot arrangements are such that the locations of high wear are eliminated as a result of the character of the final closing movement when the force on the leaflets is at its highest during closing movement.

The heart valve 11 includes 3 identical leaflets or valve members 13 which are supported within a generally annular valve body 15. The leaflets 13, which are sometimes referred to in the art as occluders, undergo what is generally referred to as pivoting or swinging movement guided by pivot arrangements which account for the supporting interengagement between the leaflets 13 and the valve body 15. The arrangement is such that the leaflets alternately open and close to either allow the smooth downstream flow of blood in the direction of the arrow labeled BF in FIG. 1 or prevent substantial regurgitation or reverse flow of blood in the opposite, upstream direction.

Figure 8:
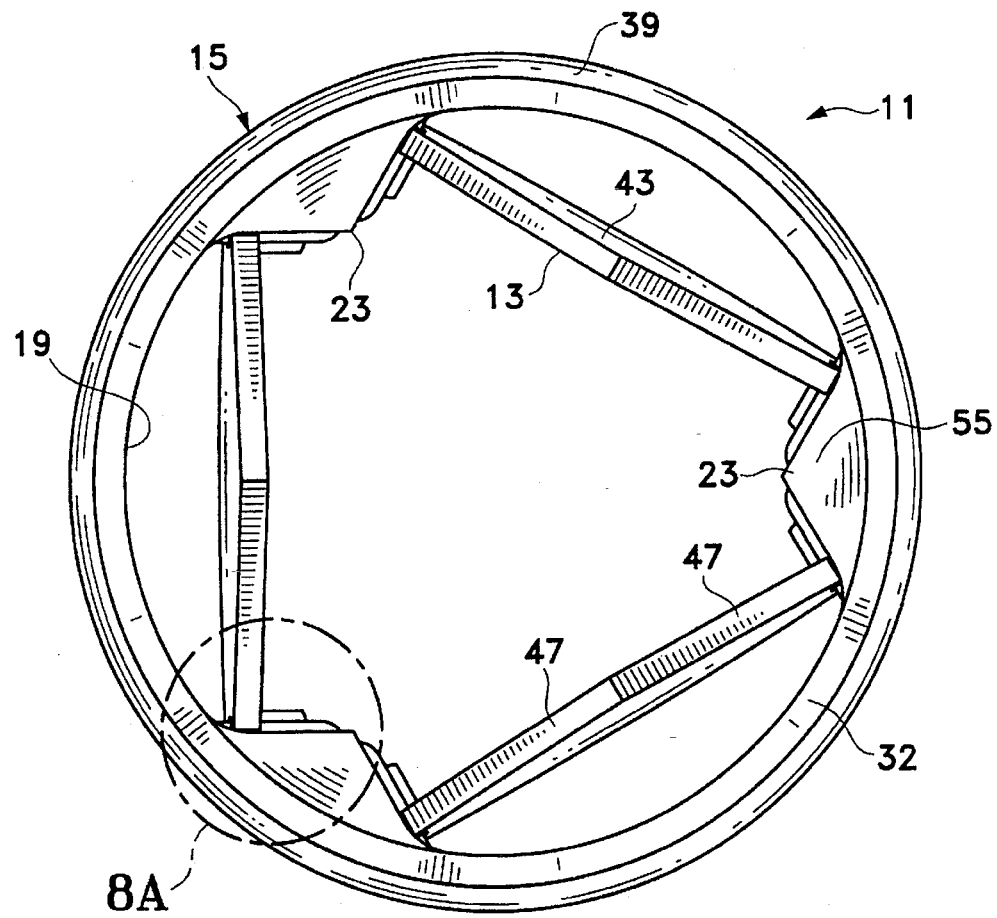
FIG. 8 is a bottom view of the valve of FIG. 1 with the leaflets in the open position with the suture ring omitted.
Figure 8A:
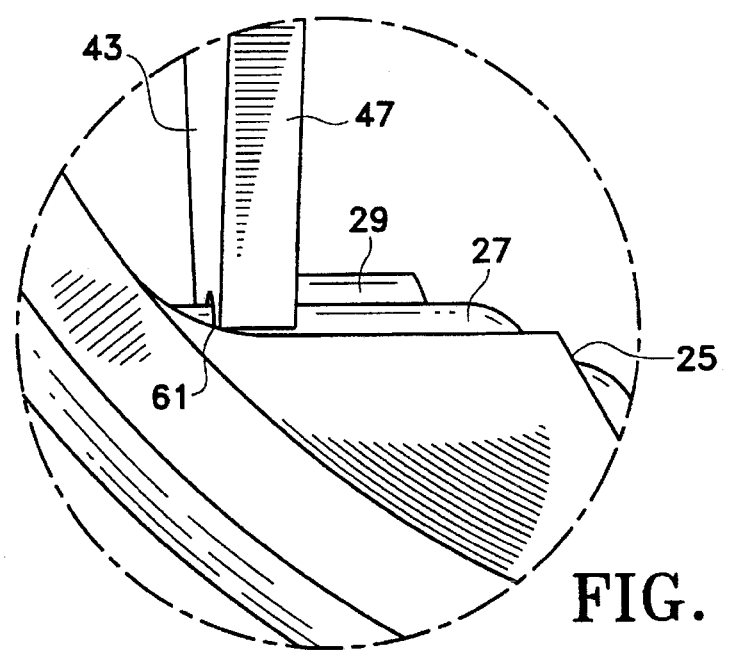
FIG. 8A is an enlarged fragmentary view showing a portion of FIG. 8.

The valve body 15 defines the blood flow passageway and has an interior wall surface 19 of nominally circular cross-section (see FIG. 8). The valve body 15 has a curved entrance region 21 at its upstream end which has been found to substantially increase streamlined flow characteristics through the valve, resulting in low turbulence and substantially no generation of thrombosis. The details of the curved entrance region 21, which extends axially for a distance not greater than about ⅓ of the average length of the valve body, are discussed hereinafter along with the operation of the valve itself.

Figure 2:
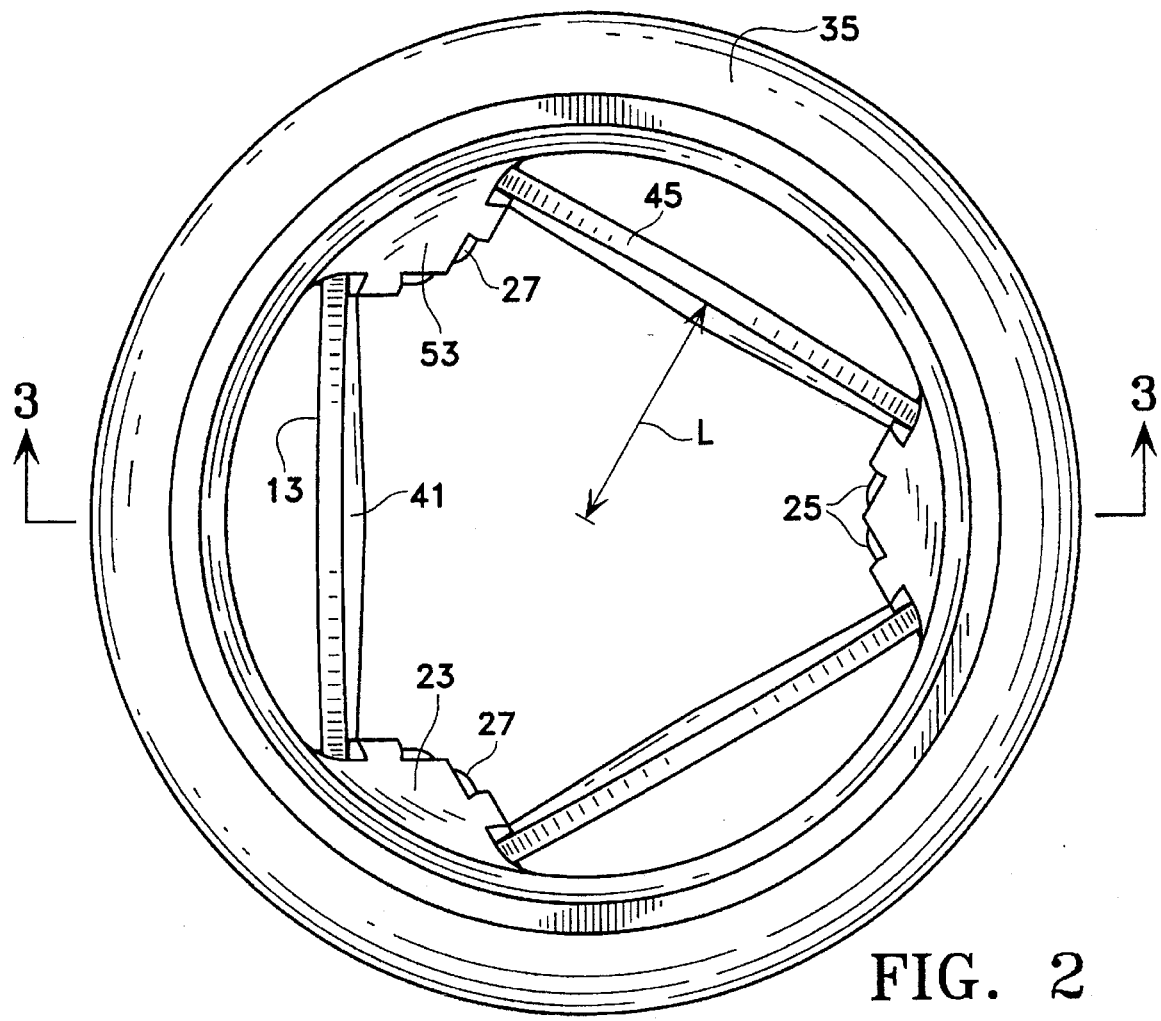
FIG. 2 is a top plan view of the trileaflet heart valve shown in FIG. 1 with the leaflets shown in their open position.
Figure 3:
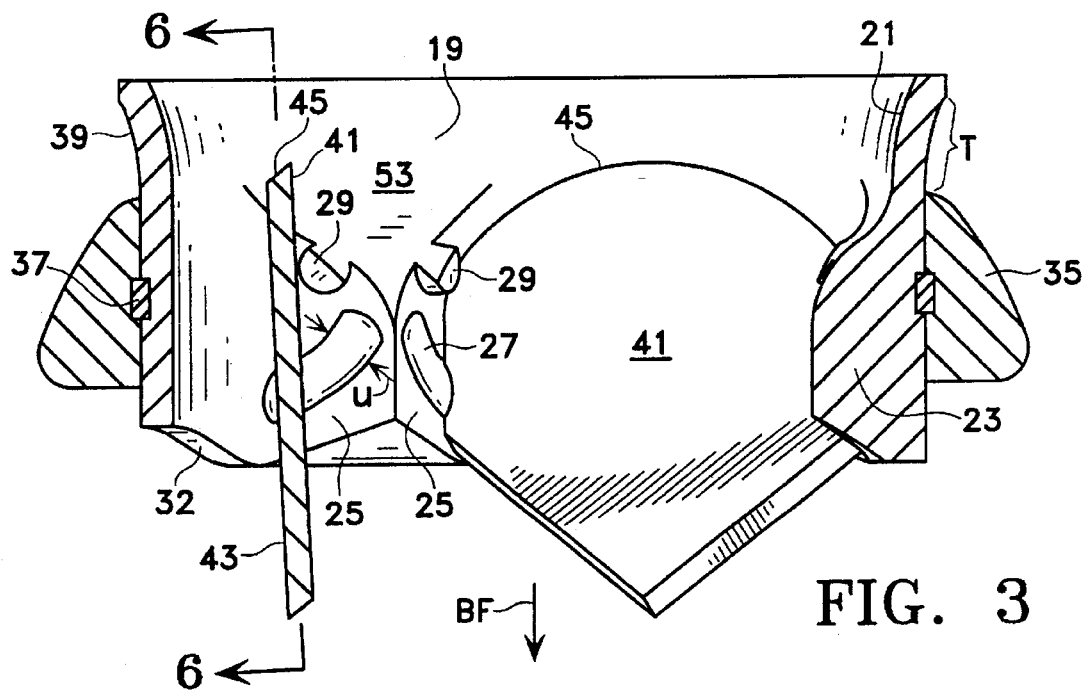
FIG. 3 is a sectional view of the trileaflet heart valve taken along the line 3—3 of FIG. 2.
Figure 4:
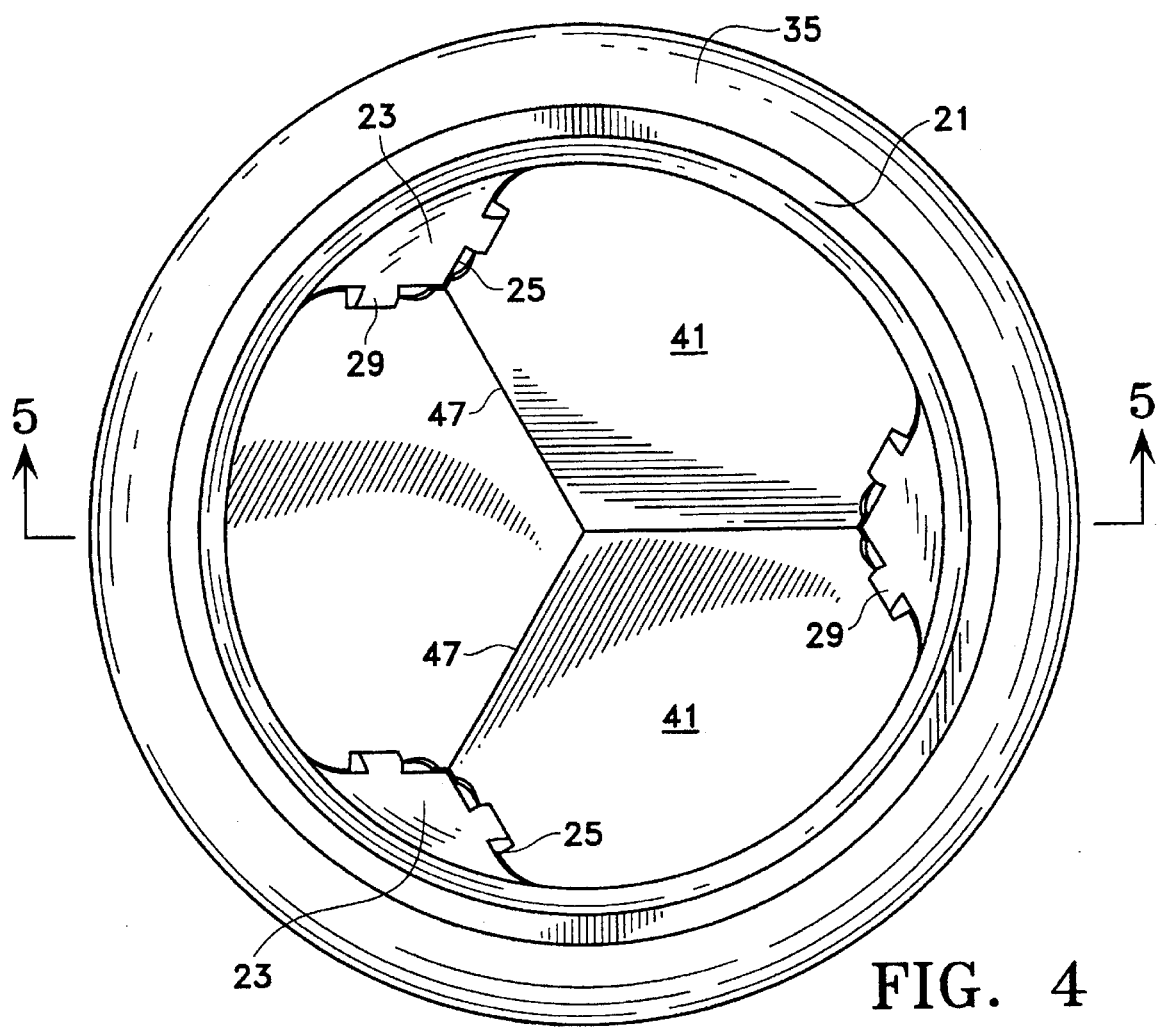
FIG. 4 is a top plan view similar to FIG. 2 with the leaflets shown in the closed position.

The valve body 15 includes 3 generally wedge-shaped projections 23 which extend radially into the central passageway at 120° intervals, as best seen in FIGS. 2 and 4. Each projection 23 has a pair of flat surface portions 25 that are aligned at about 120° to each other. Protruding outward from the face of each of these flat surface portions is a ridge or rail 27 and a short post 29 which is located generally adjacent and in association with the upstream end of the ridge 27, as best seen perhaps in FIG. 3. The ridges and posts interengage with the leaflets 13 and thus constitute ½ of the pivot arrangement that controls the opening and closing movements of the valve.

The interior surface of the valve body 15 is thus generally rectilinear throughout its major portion of its axial length downstream of the outwardly curved entrance end 21. As best seen perhaps in FIG. 5, the downstream end of the valve body 15 has a shallow scalloped configuration wherein 3 indentations or scallops 31 are formed in the regions of the circumference of the valve body at locations between radial projections 23. As a result of the scalloped construction, the valve body has a downstream edge 32 of generally undulating configuration.

Figure 5:
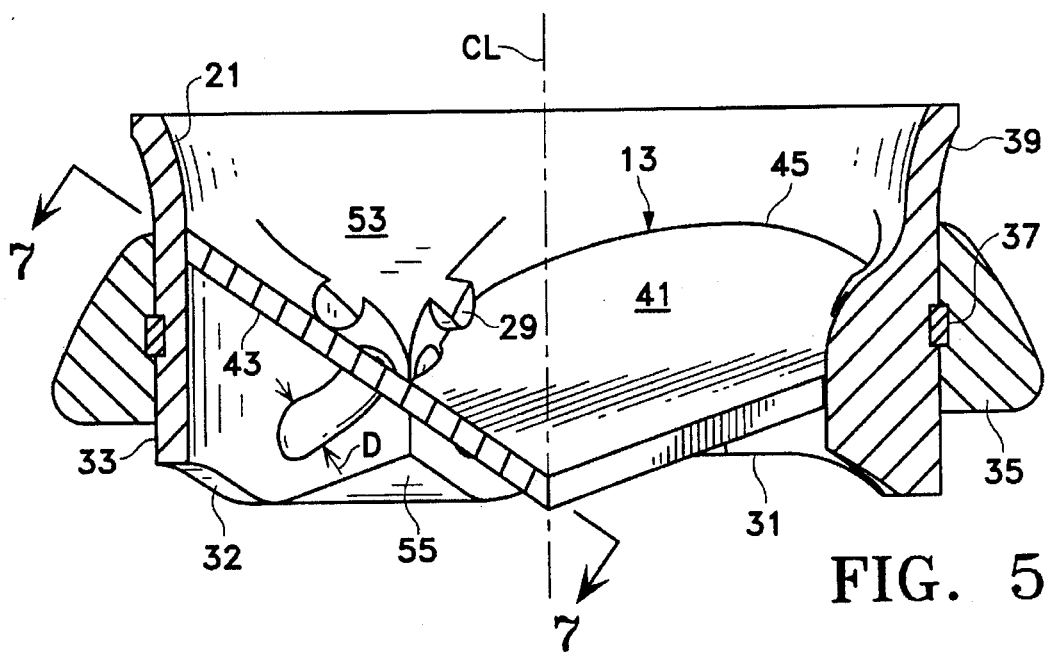
FIG. 5 is a sectional view taken generally along the line 5—5 of FIG. 4.

The valve body 15 has a right circular cylindrical exterior surface 33 in the region downstream of the entrance end, except for an interruption in the region for attaching a suture ring. A suture ring 35 is shown schematically in FIGS. 3 and 5 which is oriented for use in implanting the heart valve 11 in the aortic position, or more particularly in a supra-aortic orientation, as explained in more detail hereinafter. Accordingly shown in FIGS. 3 and 5 is a schematic representation of a mounting ring 37 which is shown as being received in an accommodating groove formed in the right circular cylindrical portion of the exterior surface and extending into the region of the suture ring itself to facilitate interconnection as is well known in this art. It should likewise be understood that the mounting ring could be equivalently formed as a protruding band which is an integral portion of the valve body itself.

The valve body 15 is preferably made of a suitable material, such as pyrocarbon or pyrocarbon-coated graphite, as is well known in this art, which has sufficient resiliency that it can be deformed so as to prevent the insertion of the individual leaflets 13 in their operative locations. Preferably the valve body is made from a graphite substrate coated with On-X™ pyrocarbon, which is available from Medical Carbon Research Institute, LLC, of Austin, Tex., and which is described in detail in U.S. patent application Ser. No. 08/303,064, filed Sep. 8, 1994 (upon which the issue fee has been paid). Detailed examples of sewing or suture rings which can be employed are described in U.S. Pat. Nos. 4,535,483 and 5,178,633, the disclosures of which are incorporated herein by reference. When the heart valve 11 is intended for implantation in the mitral position, a different shaped suture ring is appropriately used, as is well known in this art.

Because of the relatively thin wall of the heart valve body 15 and the outwardly flaring entrance region 21, the exterior surface 33 of the valve body has an upstream section 39 which is a concave section of the interior surface of a hollow torus. This construction, in addition to significantly increasing the flow through the valve passageway itself by reducing the transvalvular pressure drop, also provides a unique opportunity for implanting the illustrated heart valve in a supra-annular orientation where the suture ring 35 sits atop the remaining tissue annulus from which the defective aortic valve was excised in the patient. In such orientation, the entrance end extends through the tissue annulus so as to be accommodated in a location where the raw edge of the tissue would be in contact with the concave toroidal surface 39 of the valve body, in the region marked "T" in FIG. 3. It should be seen that this accomplishes a dual purpose. First, it maximizes the interior diameter of the nominal cylindrical interior surface 19 that defines the valve passageway, and second, it provides an outwardly flaring surface which has the effect of directing any panus that would grow from the raw edge of the tissue annulus (following implantation) in a direction outward and away from the entrance to the valve passageway where it would potentially narrow the entrance passageway and/or interfere with the operation of the leaflets.

The leaflets 13 are each identical in shape and size. Each leaflet has two rectilinear, preferably flat, surfaces, i.e. an inflow surface 41 and an outflow surface 43, and each leaflet is preferably of substantially constant thickness such that the surfaces 41 and 43 are parallel to each other. The inflow surface 41 is arbitrarily defined as the surface which faces upstream with the leaflets in the closed position (see FIG. 5), whereas the outflow surface 43 faces downstream. Although the leaflets 13 are preferably flat, other configurations, such as sections of hollow cylinders of circular or elliptical cross-section, can alternatively be employed, as discussed in more detail in U.S. Pat. No. 5,246,453, the disclosure of which is incorporated herein by reference. Alternatively, the leaflets may be curved about an axis parallel to the pivot axis or may have 3-dimensional curvature. The leaflets 13 each have a major arcuate upstream edge surface 45 which is located at the upstream edge of the leaflet in the open position as best seen in FIG. 3. The arcuate edge surface 45 preferably has a configuration such as to abut and seat closely against the cylindrical interior surface 19 of the valve body in the closed position orientation. Each leaflet also has a pair of downstream planar edge surfaces 47 which are oriented at an angle of about 120° to each other, as a result of which they mate flushly against one another, as best seen in FIG. 4, so as to close the interior passageway through the valve in the closed position. As can be seen from FIG. 5, the downstream edge surfaces 47 are oriented at an appropriate angle to the inflow and outflow surfaces 41, 43 so as to accomplish such a flush, abutting relationship in the closed position. The downstream edge surfaces 47 are accordingly oriented at an angle to the outflow surface 43 which is substantially the same as the acute angle which the inflow and outflow surfaces in the closed position form with the centerline through the valve body which is indicated by the reference CL in FIG. 5. This angle is preferably between about 30° and about 45° with the most preferred angle being shown in FIG. 5. As best seen perhaps in FIGS. 6 and 6A, the leaflets 13 each have a pair of planar lateral edge regions 49 located between the arcuate upstream edge and one of the downstream edge surfaces. The intermediate lateral edge surfaces 49 are interrupted by a pair of arcuate notches 51 wherein the ridges 27 are received when the leaflets are installed. The proportioning of the notches 51 relative to the ridges 27 is discussed in detail hereinafter.

It can be seen from FIGS. 2 and 3 that the three projections 23 which are spaced about the circumference of the valve body constitute areas of greater wall thickness; however, as can be seen, the entrance end region 21 is substantially uniform about the 360° circumference, being referred to as a radial swept surface. It is preferably a surface of a section of a torus, and its downstream end is preferably tangent to the major interior right circular cylindrical surface of the valve passageway so that the internal diameter of the torus is essentially equal to the interior diameter of the valve passageway. In order to minimize the disruption of the flow through the valve, the upstream ends of the three projections 23 are provided with angular surfaces 53 which slope in a downstream direction radially inward from the cylindrical interior wall surface as best seen perhaps in FIG. 5. Similar downstream surfaces are formed on the three projections 23; they slope radially inward and upstream from the downstream edge surface of the valve body.

The overall arrangement is such that, when viewed axially, the valve body 15 is divided into 3 identical regions each of which accommodates a single identical leaflet 13 which closes that portion of the passageway in the closed position, as viewed in FIG. 4.

Figure 6:
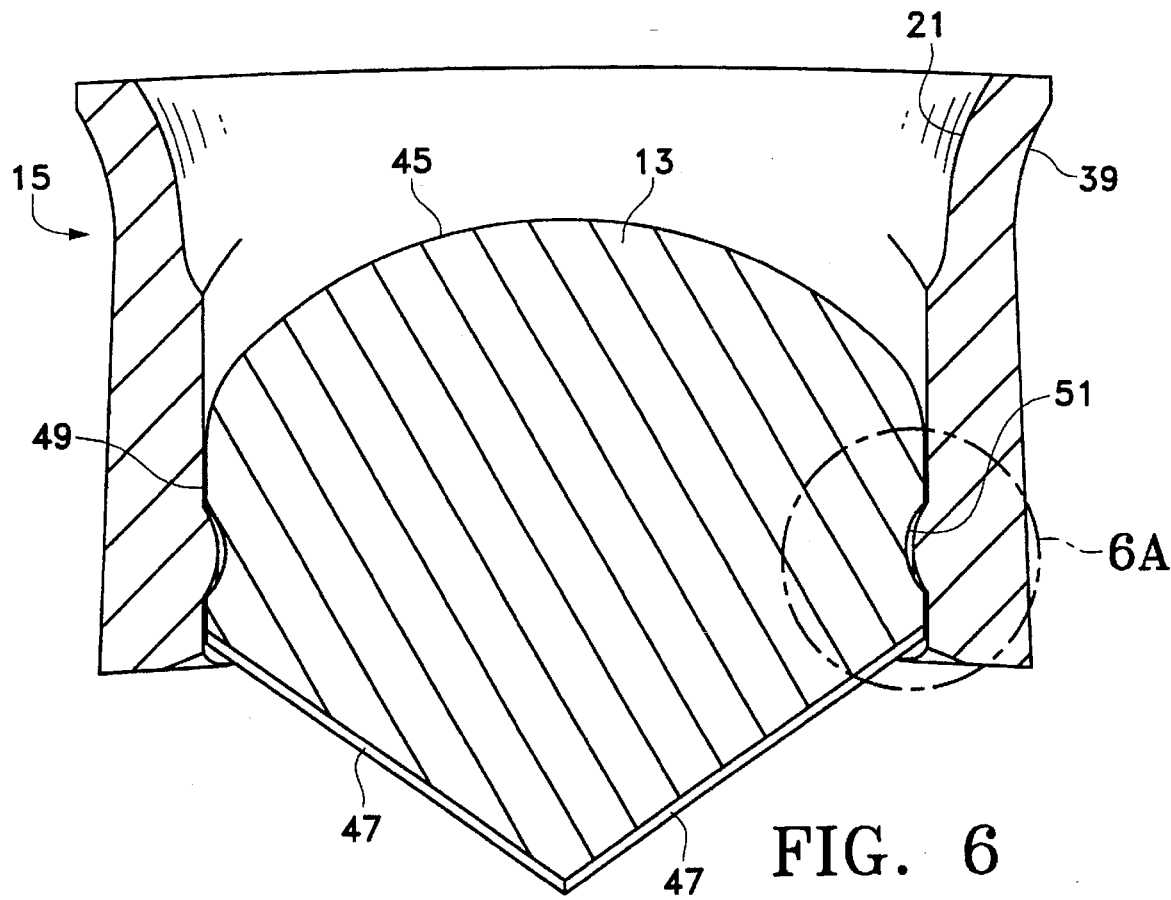
FIG. 6 is a sectional view taken generally along the line 6—6 of FIG. 3 with the suture ring omitted.
Figure 6A:
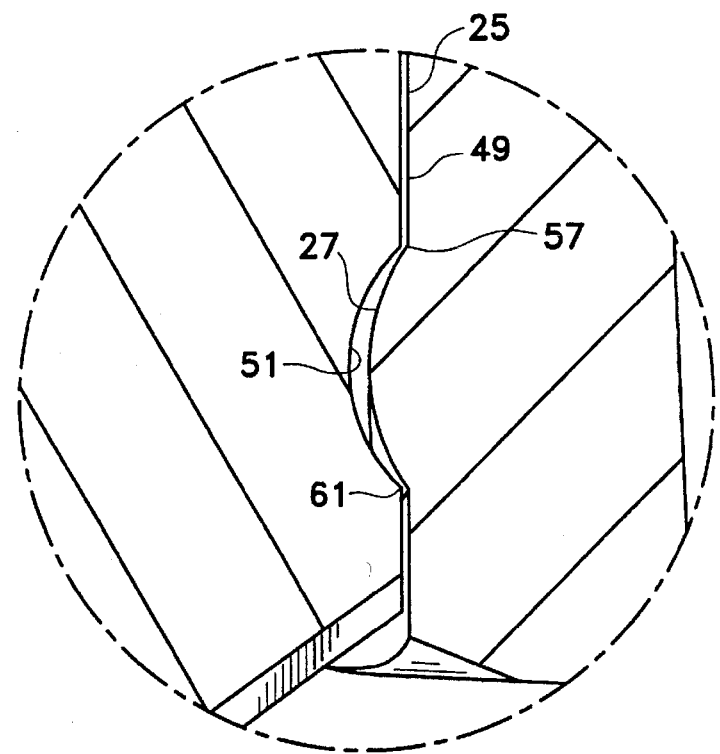
FIG. 6A is an enlarged fragmentary sectional view showing a portion of FIG. 6.

The leaflets 13 are installed in the valve body 15 in a sequential manner as by applying force such as to squeeze the valve body at diametrically opposite locations along a diameter that is generally perpendicular to the pivot axis of the leaflet being installed. The pivot axis of the leaflets in swinging from the open to the closed position is a line defined by the points of contact between the inflow surface 41 and the lateral surface of each post 29, which act as fulcrums. The posts 29 are located so that the pivot axis about which each leaflet rotates at the beginning of closing movement is spaced from the longitudinal axis a distance L equal to between about 55% and about 70% of the interior radius of the valve body. Apparatus such as illustrated in U.S. Pat. No. 5,336,259 (Aug. 9, 1994) may be used to assist in the installation of the leaflets. As can be seen from FIGS. 2 and 4, the flat surface portions 25 of the projections which flank any one of these three regions of the valve passageway are substantially parallel to each other. Squeezing along a line parallel to these wall surfaces causes them to bow outward and separate further from each other, and such further slight separation coupled with the arcuate character of the ridges allows the leaflet to be axially inserted through the outflow end of the valve body. Once the leaflet has been inserted, removal of the squeezing force allows the valve body to return to its original annular configuration providing the desired minimal clearance between the flat wall surfaces 25 of the projections and the lateral edge surfaces 49 of the leaflets. The application of the squeezing force is then sequentially shifted to a diameter 120° from the direction of first application, and the procedure is repeated two more times in order to complete the installation. Alternatively, all three leaflets can be installed at once by simultaneously applying pressure at three points 120° apart. The leaflets are preferably made of graphite substrates coated with On-X carbon as described hereinbefore with respect to the valve body. On-X carbon has physical properties such that, even with such a radially swept entrance region, it can withstand deformation such as necessary to facilitate the insertion of the leaflets in a manner such that they, in essence, snap into place over the flanking ridges that protrude outward from the flat surface portions 25 and that are of arcuate cross-section as seen in FIG. 6A.

With the heart valve 11 operatively installed in a patient and in the open position, the three leaflets 13 are designed to be able to assume an open position orientation wherein they are substantially parallel to the central longitudinal axis of the centerline through the valve body. By substantially parallel for purposes of this application is meant at an angle between 0° and about 5° from a plane which contains the pivot axis of the leaflet and is parallel to the centerline. Preferably, the leaflets in the full open position at high flow are oriented between about −1° and about +4° from a perfectly parallel orientation and most preferably are oriented at about +2° ±2°, as illustrated in FIG. 3. In this full open position depicted in FIG. 3 with blood flow through the valve passageway in a downstream direction, as depicted by the arrow labeled BF in FIG. 3, the inflow surfaces 41 of each leaflet are in contact with radially outward locations on the lateral surface of each post; as seen in FIG. 3 the locations where such contact occurs lie within the upstream one-third of the leaflet inflow surface. As previously indicated, the notches 51 fit over and straddle the arcuate cross-section ridges which protrude from the flat surfaces 25 of the pair of flanking projections 23. The ridges 27 are unique in longitudinal shape and in their variation in cross-section. They serve not only to smoothly guide the swinging leaflets along a curved path in a generally pivotal/translational movement from the open to the closed position (and vice versa), but they also constitute stops for determining the precise full open orientation of each leaflet in the positions shown in FIGS. 1, 2 and 3. As viewed in FIG. 6A, the crest of the ridge 27 constitutes its line furthest radially inward extension and the longitudinally extending surfaces above and below the crest are referred to as the upstream arcuate surface and the downstream arcuate surface.

Analysis of the forces acting upon a leaflet 13 in the full open position as shown in FIG. 3 shows that there is a significant drag force of the flowing blood along the rectilinear surfaces which is tending to move the leaflet directly downstream. This positioning is depicted in FIGS. 6 and 6A which show the leaflet, at the upstream edges 57 of the notches 51, being in contact with the upstream arcuate surface portion of the ridge 51. As can be best seen perhaps in FIG. 5, the ridges 27 are of irregular thickness so that the dimension of the ridge in the transverse direction (i.e. perpendicular to the longitudinal axis of the curved ridge which extends radially inwardly in an upstream direction) is greater near the downstream end of the ridge than near the upstream end thereof. In other words, the dimension D in FIG. 5 is greater than the dimension U in FIG. 3. As a result, the downstream end section 59 of the ridge serves as a stop for the leaflet as it swings open; more specifically, the downstream edge surface 61 of the notch eventually comes in engaging contact with the downstream arcuate surface portion of the ridge 27, which contact blocks any further movement radially outward, creating the open position stop seen in FIG. 6A. This relationship can also be seen in enlarged fragmentary view 8A.

As can be seen from FIG. 8, in the open position, an excellent large central flow channel is provided through the valve body as a result of the leaflets assuming such a substantially parallel orientation which, in combination with the outwardly flaring entrance end, results in a very low transvalvular pressure drop across the valve. Moreover, the streamlined flow which results from this configuration, and particularly from the entrance end configuration, assures that there is nonturbulent flow in the three smaller sectors of the passageway lying between the outflow surfaces 43 of each leaflet and the interior right circular cylindrical surface 19 of the valve body. This results in not only a contribution of flow through these three sectors to the overall flow through the valve passageway, but it also assures good washing of all of these surfaces to prevent any stagnation and potential sources of clotting.

As previously indicated, the combination of this particular support of the leaflets 13, together with the shape and proportioning of the valve body 15, contributes to the achievement of smooth nonturbulent flow and the absence of stasis. The toroidal curvature of the curved entrance end 21 leading to a generally cylindrical valve body of substantial overall axial length has been found to achieve this desired end, i.e. the average axial length of the valve body should preferably be at least about equal to the interior radius of the circular passageway therethrough. More specifically, the construction of a valve body which has a curved entrance transition to a tabulated cylindrical, elongated passageway has been found to provide very low pressure drop for a passageway of a given diameter. In addition to the average axial length of the valve body being preferably at least 50% of the interior diameter thereof, its flared entrance section should constitute not more than about one-third of the average axial length of the valve body and should smoothly join with the downstream cylindrical section, preferably being tangent thereto. The entrance section is preferably essentially a section of the surface of a torus which is substantially tangent to the right circular cylindrical downstream interior surface. The radius of curvature of the circle that is revolved to create the torus should be between about 28% and about 80% of the radius of the valve body, and preferably between about 40% and about 65% thereof. This overall configuration increases stiffness of the valve body and permits employment of a thinner wall thickness which translates to a larger interior diameter for the passageway and less resistance to blood flow.

When reverse or upstream flow of blood begins at the end of a pumping stroke of the left ventricle, for a valve implanted in the aortic position, the leaflets 13 are subjected to the drag forces tending to cause them to translate upstream. Simultaneously, if the orientation of the leaflets is such that they are, for example, at the preferred angle of about 2° from perfectly parallel, the backflowing blood will preferentially contact the outflow surfaces 43 of the leaflets thereby applying a closing force vector against the outflow surface. The upstream drag forces upon the leaflets result in forceful contact of the downstream edges 61 of the notches 51 against the downstream surface of the arcuate ridges 27. The ridges are designed so as to have an upstream inclination in the radially interior direction at an angle of at least about 25° to a plane perpendicular to the centerline at the location where the notch 51 engages the ridge 27 in the open position, and as a result, this forceful contact effects a camming engagement, i.e. contact which results in a force vector that promotes relative sliding movement along a surface which is inclined at a significant angle to the direction in which the force is attempting to move the object. In this instance, the drag forces are attempting to move the leaflet 13 essentially directly upstream so that this camming engagement at the downstream edge of the notch creates a force vector in a direction to cause the leaflet to move toward the interior or centerline of the valve passageway. Because the inflow surface 41 of the leaflet is in contact with the two flanking posts 29 near its upstream end, this force vector causes swinging of the leaflet about an axis defined by the two points of contact between the inflow surface 41 and the two posts. This force vector acts with a moment arm equal to the distance between the momentary pivot axis of the leaflet and the downstream edge 61 of the notch, which distance is preferably at least about 35% of the interior radius of the valve body. As a result of both of these effects, the leaflets very promptly begin to pivot or swing toward the closed position. Of course, as the swinging movement of the leaflet continues, the outflow surfaces becomes oriented more and more transverse across the path of the reverse flow of blood. As can be seen from FIG. 3, the surface area of the leaflet outflow surface 43 lying downstream of the pivot axis, as defined by the flanking posts 29, is far greater than the surface area lying upstream of the pivot axis, the force differential against the downstream section of outflow surface results in rapid swinging of the leaflets to the completely closed position shown in FIG. 5.

It can be seen from FIGS. 3 and 5 that the orientation of the curved ridges 27 is not one of an arc about the post 29, and as a result, the motion of the leaflets will not be one merely of rotation but will be a combination of translation and rotation. Thus, there will be some sliding of the inflow surfaces 41 against the post, primarily within the initial stages of the closing movement. Such sliding cooperates with the camming effect and facilitates the prompt swinging movement which quickly forces the leaflet further and further into the center of the backflowing bloodstream. During this early stage, the main forces acting on the leaflet are the drag forces tending to move the leaflet upstream. There is very little wear that occurs because of sliding between the posts and the inflow surface regions where such initial contact occurs. On the other hand, when the leaflets 13 near the fully closed position, it can be seen that the notches will be in contact with the ridges near the upstream ends thereof where the orientation is substantially that of an arc about a point on the radially outward and downstream section of the cylindrical post 29; as a result, the final movement of the leaflets is one of substantially pure rotational movement. It is during this final stage of movement that the forces against pressing the leaflets into contact with the surfaces of the posts are at their highest; thus, by restricting the final movement of the leaflets to one of substantially pure rotation, it minimizes the potential for wear occurring at these points of contact as a result of sliding movement under high pressure. By avoiding the possibility of such localized wear when the pressure across the valve is high, its longevity is very substantially improved.

In the final closed position, the differential force of the blood against the outflow surface portions lying downstream of the pivot axis as defined by the line of contact with the posts is greater than the force against the upstream surface area; thus, the leaflets are caused to seat with their arcuate upstream edges 45 abutting against the interior cylindrical surface of the valve body as shown in FIG. 5. At the same time, the planar downstream edge surfaces 47 of the leaflets abut one another as shown in FIGS. 4 and 5 and thus create a complete seal across the center of the valve passageway. Therefore, in the fully closed valve, the force of the blood against the outflow surface 43 of the leaflets is borne mainly by the flanking posts 29 and by the sidewall of the valve body where the arcuate edges 45 seat.

Figure 7:
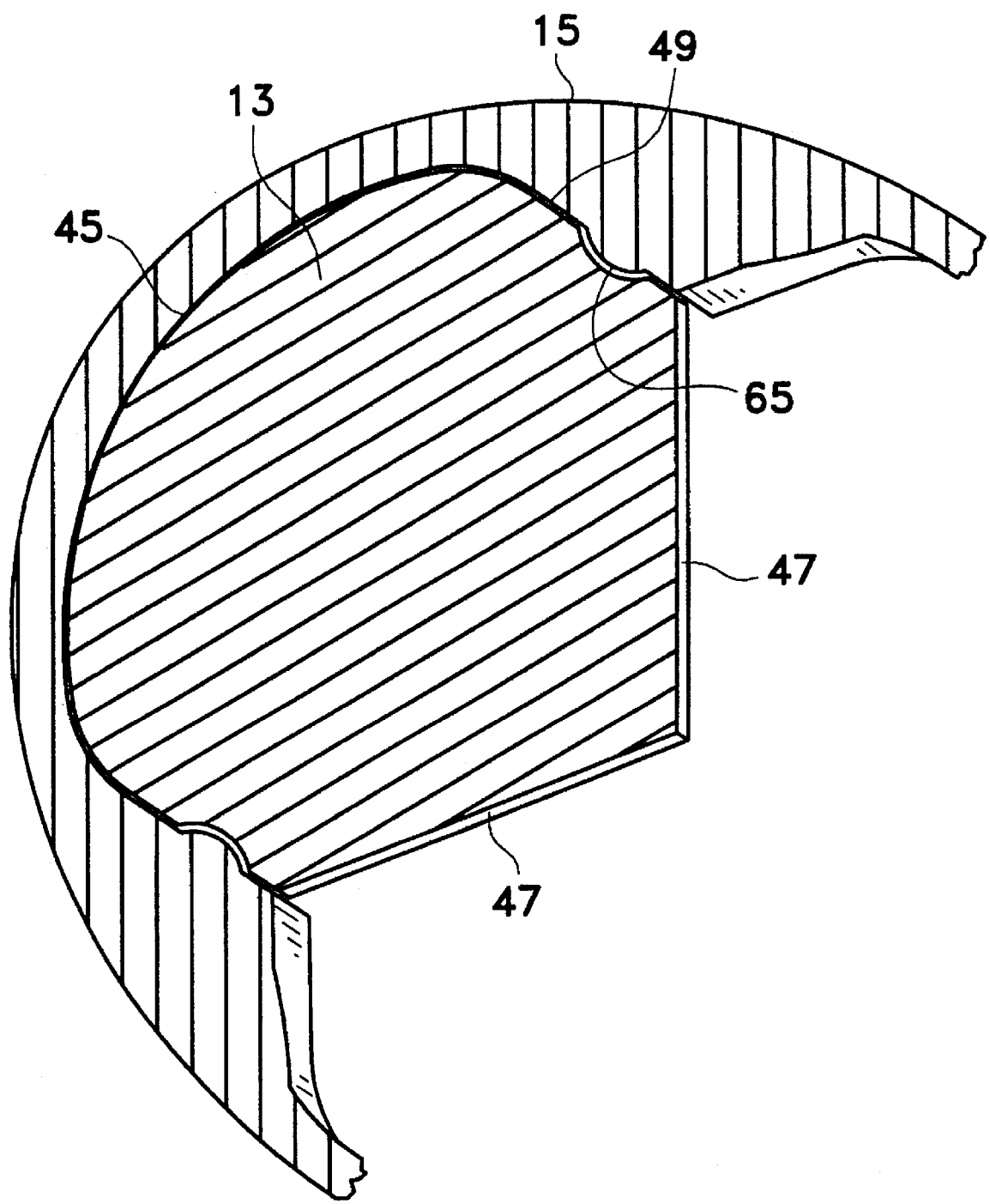
FIG. 7 is a sectional view taken along the line 7—7 of FIG. 5 with the leaflets in the closed position but with only a single leaflet being shown and with the suture ring omitted.

At the instant complete closure is achieved, the pressure of the blood against the outflow surfaces 43 of the leaflets is at its highest and results in controlled leakage through the open gaps between the interior surfaces of the notches 51 and the surface of the ridges 27, which appear as the generally crescent-shaped openings 65 shown in FIG. 7. Such leakage is controlled by controlling the height of the upstream ends of the ridges 27 relative to the depth of the arcuate notches 51 in order to create a pathway for the controlled backflow leakage. Such an arrangement concentrates the backflow leakage in the regions of the pivots where such cleansing flow serves to positively guard against the occurrence of clotting. In this respect, the average clearance or width of this generally crescent-shaped opening 65 is preferably at least about 30 microns or about 0.0012 inch.

When blood flow again reverses, as for example when the pumping stroke of the left ventricle next begins, the downstream force of the blood against the inflow surfaces 43 of the leaflets 13 causes them to swing along a radially outward curved path defined by the curved ridges 27. More particularly, the upstream edges 57 of the notches slide along the upstream surface portions of the ridges 27, with pivoting of the leaflets generally taking place along a changing axis defined generally by the contact between the notches and the ridges. Such pivoting continues until such time as the leaflets approach the substantially parallel orientation shown in FIG. 3, when contact again occurs between the inflow surfaces 41 and the posts 29. By this time, it is likely that the sliding movement of the notches will have proceeded to a location near the downstream end of the ridges, and as earlier indicated, the enlargement of the downstream end section 59 of the ridges is such that it serves as a functional stop when engaging contact occurs with the downstream edge 61 of the notch. The leaflets 13, as a result of such contact with the posts 29 and both the upstream and downstream sections of the ridges 27 at full flow have the desired substantially parallel orientation with respect to the valve centerline.

Because blood is a very delicate tissue and even minor abuses caused by turbulence and high shear can result in thrombosis or emboli generation at local regions of stagnation, it is very important that excessive turbulence coupled with high shear stresses and local regions of stasis be avoided. The foregoing valve design has been found to excellently fulfill such requirements. The employment of leaflets with flat surfaces that are free to follow and easily orient themselves substantially parallel to downstream blood flow can minimize the turbulence associated with the leaflets themselves.

By confining substantially all of the functionally engaging surfaces that define the curved paths of opening and closing movement of the leaflets to regions which are located in the main bloodstream pathway through the valve body, excellent cleansing of the components that accomplish the pivoting movement of the leaflets is assured, thus removing a major area of concern in any mechanical heart valve. By limiting the final portion of the closing movement of the leaflets to one of substantially rotation only, the likelihood of occurrence of severe localized wear at the points of contact when the force of the leaflet is near its maximum becomes greatly diminished. The overall design of the valve is such that gross hemodynamics in terms of energy loss per cardiac cycle are completely acceptable and are considered to be superior to mechanical heart valves that are presently commercially available.

Although the invention has been described with respect to certain preferred embodiments, which include what is presently considered to be the best mode for carrying out the invention, it should be understood that various changes and modifications that would be obvious to one having the ordinary skill in this art may be made without departing from the scope of the invention which is defined by the claims appended hereto. For example, as earlier indicated, the invention is not limited to occluders in the form of leaflets having flat body sections but is considered to be also applicable to leaflets having curved body sections with substantially rectilinear surfaces or even surfaces having 3-dimensional curvature. In this respect, it may be desirable to create a central passageway of still greater area through such a trileaflet valve by employing leaflets which are curved about axes parallel to the valve centerline to achieve a still greater central blood flow path through the valve body.

Particular features of the invention are emphasized in the claims which follow.

What is claimed is:

1. A trileaflet prosthetic heart valve including a generally annular valve body having an interior wall of generally circular cross-section, which wall defines a central passageway for blood flow therethrough having a central longitudinal axis extending in an upstream-downstream direction, and having three projections which extend radially into said central passageway at 120° intervals and which projections each have a pair of flat surfaces that are aligned at about 120° to each other, three cooperating leaflets, each having an arcuate upstream edge surface, a pair of downstream edge surfaces arranged at an angle of about 120° to each other, and a pair of parallel lateral edge surfaces, said leaflets being mounted in said valve body to alternate between an open position where flow of blood in a downstream direction is permitted and a closed position where flow of blood in an upstream direction is blocked, said leaflets each having opposite inflow and outflow surfaces with said inflow surface facing upstream and said outflow surface facing downstream in the closed position, and a pivot arrangement by which said leaflets are guided in moving between said open position and said closed position, which pivot arrangement permits each of said leaflets to assume an orientation substantially parallel to said central longitudinal axis in the open position during downstream blood flow and to close by pivoting therefrom upon reverse flow of blood in an upstream direction in such a manner that said downstream edges of said leaflets swing upstream toward said central longitudinal axis in moving to the closed position, said pivot arrangement comprising (a) six ridges having upstream and downstream ends and six associated upstream posts protruding from respective of said flat surfaces of each of said projections and (b) six notches formed in respective of said parallel lateral edge surfaces of said leaflets, which notches are shaped to straddle said ridges and to translate therealong, said ridges each being generally curved to define a path which extends radially inward and upstream from the downstream end thereof and said ridges being proportioned so that the downstream ends thereof are enlarged in cross-section relative to said upstream ends, said notches being proportioned so as to be oversize with respect to the cross-section of upstream ends of said ridges so that said leaflets are readily displaceable along said ridges so as to swing generally upstream along a path defined by said ridges upon the reversal of normal downstream flow of blood through the valve, and said notches also being proportioned to engage said enlarged downstream ends in a manner so as to stop each said leaflet in said substantially parallel open position orientation with said inflow surfaces in contact with said upstream posts.

2. A prosthetic heart valve according to claim 1 wherein each said ridge is arcuate in transverse cross-section and thus has longitudinally extending upstream and downstream surface portions and wherein each said notch has an upstream edge and a downstream edge, which edges respectively contact said upstream and downstream surface portions of said ridges in said open position orientation.

3. A prosthetic heart valve according to claim 2 wherein each said notch has a concave surface of a curvature similar to that of said ridge transverse arcuate cross-section.

4. A prosthetic heart valve according to claim 1 wherein each said post is located axially upstream of said associated curved ridge and in a position to interengage with said leaflet inflow surface when said leaflet is oriented substantially parallel to said longitudinal axis of said valve body in the open position orientation.

5. A prosthetic heart valve according to claim 4 wherein said leaflets have substantially rectilinear outflow and inflow surfaces.

6. A prosthetic heart valve according to claim 5 wherein said rectilinear outflow and inflow surfaces are flat and parallel to each other.

7. A prosthetic heart valve according to claim 6 wherein said two downstream edge surfaces of each said leaflet are flat and are arranged at appropriate angles to said inflow surface so that said edges of each leaflet abut respectively in surface-to-surface contact with one edge of each of the other two leaflets in the closed position.

8. A prosthetic heart valve according to claim 7 wherein each said leaflet is proportioned so that, when said downstream flat edge surfaces of said leaflets abut one another in the closed position, said inflow surfaces of said leaflets are spaced downstream from said posts.

9. A prosthetic heart valve according to claim 7 wherein said curved path defined by said ridges is such that said inflow surface slides in contact with said upstream posts during initial closing movement whereas the final swinging movement to the closed position orientation is one of substantially pure rotation.

10. A prosthetic heart valve according to claim 4 wherein each said post has a curved surface section against which said inflow surface of said leaflet abuts.

11. A prosthetic heart valve according to claim 10 wherein said curved surface section of each post acts as a fulcrum means to define a pivot axis for said pivoting leaflet.

12. A prosthetic heart valve according to claim 11 wherein said posts are located so that the pivot axis about which each said leaflet rotates at the beginning of its closing movement is spaced from said longitudinal axis a distance equal to between about 55% and about 70% of the interior radius of said valve body.

13. A prosthetic heart valve according to claim 11 wherein, upon upstream axial displacement of said leaflets as a result of reverse blood flow in an upstream direction, a camming action is exerted upon said leaflets when a downstream edge of said notch engages a downstream surface of said ridge, which camming action is effective to cause each said leaflet to immediately begin to swing toward its closed position orientation, said ridge downstream surface in the region of said enlarged downstream end being oriented at an angle of at least about 25° to a plane perpendicular to said longitudinal axis.

14. A prosthetic heart valve according to claim 13 wherein said pivot axis is spaced a distance upstream from the point of said camming contact that is equal to at least about 35% of the interior radius of said valve body.

15. A trileaflet prosthetic heart valve including a generally annular valve body having a smoothly flared upstream entrance end which leads to an interior wall of generally circular cross-section, which wall defines a central passageway for blood flow therethrough having a central longitudinal axis extending in an upstream-downstream direction, and having three projections which extend radially into said central passageway at 120° intervals, said projections each having a pair of flat surfaces that are aligned at about 120° to each other, said entrance end having an interior convex surface with a radius of curvature equal to between about 28% and about 80% of said central passageway radius, three cooperating leaflets, each having an arcuate upstream edge surface, a pair of downstream edge surfaces, and a pair of parallel lateral edge surfaces, said leaflets being mounted in said valve body to alternate between an open position where flow of blood in a downstream direction is permitted and a closed position where flow of blood in an upstream direction is blocked, said leaflets each having opposite inflow and outflow surfaces with said inflow surface facing upstream and said outflow surface facing downstream in the closed position, and a pivot arrangement by which said leaflets are guided in moving between said open position and said closed position, which pivot arrangement permits each of said leaflets to assume an orientation substantially parallel to said central longitudinal axis in the open position during downstream blood flow and to close by pivoting therefrom upon reverse flow of blood in an upstream direction in such a manner that said downstream edges of said leaflets swing upstream toward said central longitudinal axis in moving to the closed position, said pivot arrangement comprising ridges having upstream and downstream ends and associated upstream posts protruding from respective of said flat surfaces of each of said projections and notches formed in said parallel lateral edge surfaces of said leaflets, which notches are shaped to straddle said ridges and to translate therealong, said ridges each being generally curved to define a path which extends radially inward and upstream from the downstream end thereof and said ridges being proportioned so that the downstream ends thereof are enlarged in cross-section relative to said upstream ends, said notches being proportioned so as to be oversize with respect to the cross-section of upstream ends of said ridges so that said leaflets are readily displaceable along said ridges so as to swing generally upstream along a path defined by said ridges upon the reversal of normal downstream flow of blood through the valve, and said notches also being proportioned to engage said enlarged downstream ends in a manner so as to stop each said leaflet in said substantially parallel open position orientation with said inflow surfaces in contact with said upstream posts.

16. A prosthetic heart valve according to claim 15 wherein each said ridge is arcuate in transverse cross-section and thus has longitudinally extending upstream and downstream surface portions and wherein each said notch has an upstream edge and a downstream edge, which edges respectively contact said upstream and downstream surface portions of said ridges in said open position orientation.

* * * * *